(12) United States Patent
Kishimoto et al.

(10) Patent No.: US 7,247,424 B2
(45) Date of Patent: Jul. 24, 2007

(54) SCREENING METHOD FOR A SUBSTANCE HAVING HYPOGLYCEMIC ACTIVITY BY USING STAT-INDUCED INHIBITOR OF STAT FUNCTION-1

(75) Inventors: Tadamitsu Kishimoto, Tondabayashi (JP); Tetsuji Naka, Toyonaka (JP)

(73) Assignee: Tadamitsu Kishimoto, Osaka (JP)

( * ) Notice: Subject to any disclaimer, the term of this patent is extended or adjusted under 35 U.S.C. 154(b) by 0 days.

(21) Appl. No.: 10/363,930

(22) PCT Filed: Sep. 11, 2001

(86) PCT No.: PCT/JP01/07879

§ 371 (c)(1),
(2), (4) Date: Mar. 10, 2003

(87) PCT Pub. No.: WO02/22813

PCT Pub. Date: Mar. 21, 2002

(65) Prior Publication Data

US 2003/0186215 A1    Oct. 2, 2003

(30) Foreign Application Priority Data

Sep. 11, 2000    (JP)    ............... 2000-274531

(51) Int. Cl.
*C12Q 1/00*    (2006.01)
*C12N 5/06*    (2006.01)
*C12N 5/16*    (2006.01)

(52) U.S. Cl. .................... 435/4; 435/325; 435/352

(58) Field of Classification Search ............... 435/4, 435/29, 325, 357
See application file for complete search history.

(56) References Cited

U.S. PATENT DOCUMENTS 4,440,860 A * 4/1984 Klagsbrun ................ 435/384
6,514,725 B1 * 2/2003 Kishimoto et al. ........ 435/69.1

FOREIGN PATENT DOCUMENTS

EP    989186 A1    3/2000

OTHER PUBLICATIONS

Kawazoe Y. et al., "Signal Transducer and Activator of Transcription (STAT)-induced STAT Inhibitor 1 (SSI-1)/Suppresor of Cytokine Signaling 1(SOCS1) Inhibits Insulin Signal Transduction Pathway through Modulating Insulin Receptor Substrate 1(IRS-1) Phosphorylation", J. Exp. Med., Jan. 2001, vol. 193, No. 2, pp. 263 to 270.
Emanuelli B. et al., "SOCS-3 Is an Insulin-induced Negative Regulator of Insulin Signaling", J. Biol. Chem., May 2000, vol. 275, No. 21, pp. 15985 to 15991.
Zong C. S. et al., "Mechanism of STAT3 Activation by Insulin-like Growth Factor I Receptor", J. Biol. Chem., May 2000, vol. 275, No. 20, pp. 15099 to 15105.
Naka T. et al., "Structure and Function of a New STAT-induced STAT Inhibitor", Nature, (1997), vol. 387, pp. 924 to 929.
Minamoto S. et al., "Cloning and Functional Analysis of New Members of STAT Induced STAT Inhibitor (SSI) Family: SSI-2 and SSI-3", Biochem. Biophys. Res. Commun., (1997) vol. 237, No. 1, pp. 79 to 83.
Gual P. et al., "Interaction of Janus Kinases JAK-1 and JAK-2 with the Insulin Receptor and the Insulin-Like Growth Factor-1 Receptor", Endocrinology, (1998), vol. 139, No. 3, pp. 884 to 893.
Narazaki M. et al., "Three Distinct Domains of SSI-1/SOCS-1/JAB Protein Are Required for its Suppression of Interleukin 6 Signaling", Proc. Natl. Acad. Sci. USA, (1998), vol. 95, pp. 13130 to 13134.
Naka T. et al., "Accelerated Apoptosis of Lymphocytes By Augmented Induction of Bax in SSI-1 (STAT-induced STAT Inhibitor-1) Deficient Mice", Proc. Natl. Acad. Sci. USA, (1998), vol. 95, pp. 15577 to 15582.
Paz K. et al., "A Molecular Basis for Insulin Resistance", J. Biol. Chem., (1997), vol. 272, No. 47, pp. 29911 to 29918.
Masashi Yamamoto edition, "Jikken Igaku Bessatsu BioScience Yougo Library; Saibou-nai Signal Dentatsu", Kabushiki Kaisha Youdosha, May 20, 1998, pp. 126 to 127.
Kawazoe Y. et al.: "SSI/SOCS family proteins are involved in the negative regulation for various signal transduction pathway" CYTOKINE, Nov. 1999, p. 935, vol. 11, No. 11.
Kieszkiewicz J.E. et al.: "Hyperglycemia induces the expression of suppressor of cytokine signaling genes in proximal tubular cells" Journal of the American Society of Nephrology, vol. 11, Sep. 2000, p. 645A.
Mooney R.A. et al.: "Suppressors of cytokine signaling-1 and -6 associate with and inhibit the insulin receptor: A potential mechanism for cytokine-mediated insulin resistance" Journal of Biological Chemistry, vol. 276, No. 28, Jul. 13, 2001, pp. 25889-25893.
Naka T. el al.: "Negative regulation of cytokine signaling: STAT-induced STAT inhibitor" Tibs Trends in Biochemical Sciences, Elsevier Publication, Cambridge, EN, vol. 24, No. 10, Oct. 1999, pp. 394-398.
Dey B.R. et al.: "Interaction of human suppressor of cytokine signaling (SOCS)-2 with the insulin-like growth factor-1 receptor" Science, American Association for the Advancement of Science, US, vol. 273, No. 37, Sep. 11, 1998, pp. 24095-24101.

* cited by examiner

*Primary Examiner*—Vera Afremova
(74) *Attorney, Agent, or Firm*—Sughrue Mion, PLLC (57) ABSTRACT

The present invention discloses a screening method for a substance, which could be a therapeutic agent for diabetes with insulin resistance through regulating a function of a molecule involved in insulin signaling pathway. More specifically, the present invention discloses a screening method for a substance having hypoglycemic activity, which is characterized by contacting a sample to STAT-induced inhibitor of STAT function-1 in the presence of insulin, and by detecting inhibitory activity of STAT-induced inhibitor of STAT function-1 by a substance in the sample, as an index.

6 Claims, 5 Drawing Sheets

SEQUENCE LISTING

```
<160> NUMBER OF SEQ ID NOS: 2

<210> SEQ ID NO 1
<211> LENGTH: 1087
<212> TYPE: DNA
<213> ORGANISM: Mus musculus
<220> FEATURE:
<221> NAME/KEY: CDS
<222> LOCATION: (16)..(651)

<400> SEQUENCE: 1
ggcccctcga gtagg atg gta gca cgc aac cag gtg gca gcc gac aat gcg        51
               Met Val Ala Arg Asn Gln Val Ala Ala Asp Asn Ala
                 1               5                  10 atc tcc ccg gca gca gag ccc cga cgg cgg tca gag ccc tcc tcg tcc        99
Ile Ser Pro Ala Ala Glu Pro Arg Arg Arg Ser Glu Pro Ser Ser Ser
         15                  20                  25 tcg tct tcg tcc tcg cca gcg gcc ccc gtg cgt ccc cgg ccc tgc ccg       147
Ser Ser Ser Ser Ser Pro Ala Ala Pro Val Arg Pro Arg Pro Cys Pro
     30                  35                  40 ggg gtc cca gcc cca gcc cct ggc gac act cac ttc cgc acc ttc cgc       195
Gly Val Pro Ala Pro Ala Pro Gly Asp Thr His Phe Arg Thr Phe Arg
45                  50                  55                  60 tcc cac tcc gat tac cgg cgc atc acg cgg acc agc gcg ctc ctg gac       243
Ser His Ser Asp Tyr Arg Arg Ile Thr Arg Thr Ser Ala Leu Leu Asp
                 65                  70                  75 gcc tgc ggc ttc tat tgg gga ccc ctg agc gtg cac ggg gcg cac gag       291
```

-continued

```
cgg ctg cgt gcc gag ccc gtg ggc acc ttc ttg gtg cgc gac agt cgc     339
Arg Leu Arg Ala Glu Pro Val Gly Thr Phe Leu Val Arg Asp Ser Arg
         95                 100                 105 caa cgg aac tgc ttc ttc gcg ctc agc gtg aag atg gct tcg ggc ccc     387
Gln Arg Asn Cys Phe Phe Ala Leu Ser Val Lys Met Ala Ser Gly Pro
    110                 115                 120 acg agc atc cgc gtg cac ttc cag gcc ggc cgc ttc cac ttg gac ggc     435
Thr Ser Ile Arg Val His Phe Gln Ala Gly Arg Phe His Leu Asp Gly
125                 130                 135                 140 aac cgc gag acc ttc gac tgc ctt ttc gag ctg ctg gag cac tac gtg     483
Asn Arg Glu Thr Phe Asp Cys Leu Phe Glu Leu Leu Glu His Tyr Val
             145                 150                 155 gcg gcg ccg cgc cgc atg ttg ggg gcc ccg ctg cgc cag cgc cgc gtg     531
Ala Ala Pro Arg Arg Met Leu Gly Ala Pro Leu Arg Gln Arg Arg Val
         160                 165                 170 cgg ccg ctg cag gag ctg tgt cgc cag cgc atc gtg gcc gcc gtg ggt     579
Arg Pro Leu Gln Glu Leu Cys Arg Gln Arg Ile Val Ala Ala Val Gly
    175                 180                 185 cgc gag aac ctg gcg cgc atc cct ctt aac ccg gta ctc cgt gac tac     627
Arg Glu Asn Leu Ala Arg Ile Pro Leu Asn Pro Val Leu Arg Asp Tyr
190                 195                 200 ctg agt tcc ttc ccc ttc cag atc tgaccggctg ccgctgtgcc gcagcattaa    681
Leu Ser Ser Phe Pro Phe Gln Ile
205                 210 gtggggcgc  cttattattt  cttattatta  attattatta  tttttctgga  accacgtggg   741
agccctcccc  gcctgggtcg  gagggagtgg  ttgtggaggg  tgagatgcct  cccacttctg   801
gctggagacc  tcatcccacc  tctcaggggt  ggggtgctc   ccctcctggt  gctccctccg   861
ggtcccccct  ggttgtagca  gcttgtgtct  ggggccagga  cctgaattcc  actcctacct   921
ctccatgttt  acatattccc  agtatctttg  cacaaaccag  gggtcgggga  gggtctctgg   981
cttcattttt  ctgctgtgca  gaatatccta  tttatatttt  ttacagccag  tttaggtaat  1041
aaactttatt  atgaaagttt  ttttttaaaa  gaaacaaaca  aagatt                  1087
```

<210> SEQ ID NO 2
<211> LENGTH: 212
<212> TYPE: PRT
<213> ORGANISM: Mus musculus

<400> SEQUENCE: 2

```
Met Val Ala Arg Asn Gln Val Ala Ala Asp Asn Ala Ile Ser Pro Ala
1               5                   10                  15

Ala Glu Pro Arg Arg Ser Glu Pro Ser Ser Ser Ser Ser Ser Ser Ser
            20                  25                  30

Ser Pro Ala Ala Pro Val Arg Pro Arg Pro Cys Pro Gly Val Pro Ala
        35                  40                  45

Pro Ala Pro Gly Asp Thr His Phe Arg Thr Phe Arg Ser His Ser Asp
    50                  55                  60

Tyr Arg Arg Ile Thr Arg Thr Ser Ala Leu Leu Asp Ala Cys Gly Phe
65                  70                  75                  80

Tyr Trp Gly Pro Leu Ser Val His Gly Ala His Glu Arg Leu Arg Ala
                85                  90                  95

Glu Pro Val Gly Thr Phe Leu Val Arg Asp Ser Arg Gln Arg Asn Cys
            100                 105                 110

Phe Phe Ala Leu Ser Val Lys Met Ala Ser Gly Pro Thr Ser Ile Arg
```

-continued

```
            115                 120                 125
Val His Phe Gln Ala Gly Arg Phe His Leu Asp Gly Asn Arg Glu Thr
    130                 135                 140

Phe Asp Cys Leu Phe Glu Leu Leu Glu His Tyr Val Ala Ala Pro Arg
145                 150                 155                 160

Arg Met Leu Gly Ala Pro Leu Arg Gln Arg Arg Val Arg Pro Leu Gln
                165                 170                 175

Glu Leu Cys Arg Gln Arg Ile Val Ala Ala Val Gly Arg Glu Asn Leu
            180                 185                 190

Ala Arg Ile Pro Leu Asn Pro Val Leu Arg Asp Tyr Leu Ser Ser Phe
        195                 200                 205

Pro Phe Gln Ile
        210
```

SCREENING METHOD FOR A SUBSTANCE HAVING HYPOGLYCEMIC ACTIVITY BY USING STAT-INDUCED INHIBITOR OF STAT FUNCTION-1

TECHNICAL FIELD OF THE INVENTION

The present invention relates to a screening method for a substance having hypoglycemic activity which is characterized by contacting a sample to STAT-induced inhibitor of STAT function-1 in the presence of insulin, and by detecting inhibitory activity of STAT-induced inhibitor of STAT function-1 by a substance in the sample, as an index.

BACKGROUND OF THE INVENTION

STAT (Signal Transducer and Activator of Transcription) is a molecule that is activated by stimulation with cytokine(s). STAT-induced inhibitor of STAT function-1 is a protein that is induced by STAT and inhibits cytokine signaling through suppressing activation of Janus Kinase (JAK). STAT-induced inhibitor of STAT function-1 (hereinafter, simply referred to as "SSI-1", though the abbreviation "SSI-1", "SOCS-1" or "SIIS-1" have been used) was first isolated from mouse by the inventors of the present invention (PCT Publication No. WO98/30688 and Naka, T. et al, Nature, 387, 924-929 (1997)). So far, eight members of the SSI family molecule, including SSI-2 and SSI-3 (Minamoto, S. et al., Biochem. Biophys. Res. Commun., 237, 79-83 (1997)),have been identified as an inhibitor. The inventors of the present invention have also already isolated human SSI-1 (Minamoto, S. et al., Biochem. Biophys. Res. Commun., 237, 79-83 (1997)).

The functional domain of SSI-1 was determined by an experiment using mutant genes of SSI-1 (Narazaki, M. et al., Proc. Natl. Acad. Sci. U.S.A., 95, 13130-13134 (1998)). More specifically, it is known that 24 amino acid residues existing in N-terminus of SH2 domain (pre-SH2) as well as SH2 domain are essential for the suppression of phosphorylation of JAK, and that SSI-1 associates to JAK through its SH2 and pre-SH2 domains. Moreover, part of the biological function of SSI-1 in vivo has been identified by the inventors of the present invention using SSI-1-deficient mice. In SSI-1-deficient mice, apoptosis was detected in several organs such as lymphocytes, heart and liver, in which SSI-1 was expressed as the ages passed, indicating that SSI-1 closely relates to survival of a cell, especially to an inflammation (Naka, T. et al., Proc. Natl. Acad. Sci. U.S.A., 95, 15575-15582 (1998)).

There are many signaling pathways in a cell, including ones induced by hormones and the like as well as cytokines. For example, insulin is a hormone relating to cell proliferation, the uptake and metabolism of glucose, the synthesis and storage of neutral fat, and protein synthesis. Insulin mediates its biological effects through its specific receptor, insulin receptor (IR). It is known that IR has an intrinsic tyrosine kinase activity and participates in the phosphorylation of insulin receptor substrate 1 (IRS-1) (Paz, K. et al., J. Biol. Chem., 272,29911-29918(1997)). Phosphorylated IRS-1 mediates various biological activities (White, M. F., Diabetologia, 40(Suppl.), S2-S17 (1997) and Myers, M. G. et al., Trens Biochem. Sci. 19 (7), 289-293 (1994)). It is also reported that JAK as well as IR was activated by insulin stimulation, suggesting an involvement of JAK in insulin signaling pathway (Giorgetti-Peraldi, S. et al., Eur. J. Biochem., 234 (2), 656-660 (1995) and Gual, P. et al., Endocrinology, 139 (3), 884-893 (1998)).

However, insulin signaling pathway has not yet been specified, and all molecules involved in the pathway have not yet been identified. It is considered that most of insulin resistant diabetes (which is characterized by normal insulin secretion but hyperinsulinemea and hyperglycemia due to low efficiency of blood sugar incorporation in peripheral tissues because of the low reactivity to insulin) is caused by the functional deficiency of IR. The cause of the disease, however, have not yet been specified and there are no established therapeutics or agents so far.

As mentioned above, the identification of molecules involved in insulin signaling pathway and agents for insulin resistant diabetes through regulating the function of those molecules has been desired. A subject of the present invention is to provide a method for screening a SSI-1 inhibitor that is a molecule capable of inhibiting intracellular insulin signaling.

DISCLOSURE OF THE INVENTION

The inventors of the present invention have directed their attention and carried out energetic researches in order to solve the above subject. As a result, the inventors have found that the blood sugar level of SSI-1 knocked-out mice was significantly lower than that of wild type mice, and that SSI-1 inhibited insulin signal transduction in SSI-1 knocked-out cells derived from SSI-1 knocked-out mice. Finally, the inventors have successfully invented a method for detecting a substance having hypoglycemic activity by using phenomena derived from SSI-1 inhibition as an index. The present invention has been completed based on these findings.

Accordingly, an aim of the present invention is to provide a method for screening a substance that has hypoglycemic activity through inhibiting SSI-1 and could be a therapeutic agent for diabetes with insulin resistance.

Next, in order to make an understanding of the present invention easier, the fundamental features and preferred embodiments of the present invention will be described first.

1. A screening method for a substance having hypoglycemic activity which is characterized by contacting a sample to STAT-induced inhibitor of STAT function-1 in the presence of insulin, and by detecting inhibitory activity of STAT-induced inhibitor of STAT function-1 by a substance in the sample, as an index.

2. The method according to (1), which is characterized by contacting a sample to cells expressing STAT-induced inhibitor of STAT function-1 in the presence of insulin, and by detecting inhibitory activity of STAT-induced inhibitor of STAT function-1 expressed by said cells by a substance in the sample, as an index.

3. The method according to (1), which comprises: (a) providing cells which express STAT-induced inhibitor of STAT function-1; (b) culturing said cells in an insulin-containing medium having added thereto a sample; (c) assessing the proliferation rate of said cells; and (d) detecting a substance having hypoglycemic activity by using the proliferation rate of said cells as an index.

4. The method according to (3), wherein said cells which express STAT-induced inhibitor of STAT function-1 are transfectants which over-express STAT-induced inhibitor of STAT function-1.

The aims, features and benefits of the present invention will be clarified through the following detailed description of the invention with figures and claims.

DETAILED DESCRIPTION OF THE INVENTION

First, in order to clarify the fundamental features of the present invention, the technical features involved in the present invention will be explained with the details resulted in completion of the present invention.

A method of the present invention for screening a substance having hypoglycemic activity is based on the inhibitory effect of SSI-1 on insulin signal transduction.

SSI-1 Does:
(1) Not bind to insulin receptor,
(2) Not inhibit kinase activity of insulin receptor,
(3) Inhibit phosphorylation of JAK kinase associated to insulin receptor,
(4) Inhibit phosphorylation of insulin receptor substrate-1 by insulin receptor, and
(5) Consequently inhibit insulin signal transduction.

SSI-1 Inhibits Insulin Signal Transduction (5).

As described above, the inventors found first that the blood sugar level was low in the SSI-1 knocked-out mice, and took note of the possibility that SSI-1 might be involved in insulin signal transduction. More specifically, embryonic fibroblast cells derived from SSI-1 knocked-out mice were isolated and observed their differentiation into adipocytes by insulin stimulation. It is known that the differentiation of mouse embryonic fibroblast cells into adipocytes is stimulated by insulin. Accordingly, the inventors speculated that the differentiation of embryonic fibroblast cells derived from SSI-1 knocked-out mice might be stimulated compared with that derived from normal mice, if SSI-1 functioned as a inhibitory molecule on insulin signal transduction. It was confirmed by the results that embryonic fibroblast cells derived from SSI-1 knocked-out mice showed burst induction of differentiation into adipocytes. It also became obvious that the sensitivity of SSI-1 knocked-out mice to insulin were augmented.

SSI-1 Inhibits Phosphorylation of Insulin Receptor Substrate-1 by insulin receptor (4).

Next, in order to elucidate the inhibitory mechanism of SSI-1 on insulin signaling, the phosphorylation of insulin receptor substrate-1 (IRS-1) under insulin stimulation was analyzed using mouse fibroblast cell line over-expressing SSI-1 (transfectant in which SSI-1 cDNA was introduced). As a result, the phosphorylation of IRS-1 after insulin stimulation was reduced in the SSI-1 over-expressing mouse fibroblast cells. In contrast, intense phosphorylation of IRS-1 after insulin stimulation was lasted in the embryonic fibroblast cells derived from SSI-1 knocked-out mice. These results indicated that SSI-1 regulates insulin signaling through phosphorylation of IRS-1.

SSI-1 Neither Bind to Insulin Receptor (1), Nor Inhibit Kinase Activity of Insulin Receptor (2).

A level of tyrosine phosphorylation of insulin receptor was analyzed in each transfectant, in which SSI-1, insulin receptor (IR), or both SSI-1 and IR cDNA was introduced. As a result, the interaction between SSI-1 and IR was not identified, and SSI-1 did not inhibit kinase activity of IR. SSI-1 inhibits phosphorylation of JAK kinase associated to insulin receptor (3).

A level of tyrosine phosphorylation of IRS-1 was analyzed in each transfectant, in which IRS-1, both IRS-1 and JAK kinase (hereinafter, simply referred to as "JAK"), or IRS-1, JAK and SSI-1 cDNA was introduced, respectively. As a result, the interaction between IRS-1 and JAK was confirmed, and the inhibition of tyrosine phosphorylation of JAK by SSI-1 was identified. In insulin signaling pathway, it is suggested that JAK associates insulin receptor and is phosphorylated through phosphorylation of insulin receptor, and that phosphorylation of JAK results in phosphorylation of IRS-1. Accordingly, it is concluded that the inhibition of phosphorylation of JAK by SSI-1 is one of causes of inhibitory mechanism of insulin signaling by SSI-1.

As obvious from the results above, it became clear that SSI-1, which was cloned first as an antagonistic molecule in inflammatory cytokine signaling, unexpectedly related to the hormone insulin. Thus it is suggested that the excess inhibition of insulin signaling by SSI-1 is one of the causes of insulin resistant diabetes. Accordingly, a compound that inhibits/regulates SSI-1 could be a fundamental and very useful therapeutic means for insulin resistant diabetes, as it can regulate insulin signaling directly.

The present invention will be described in more detail as follows.

A screening method of the present invention is the screening method for a substance having hypoglycemic activity which is characterized by contacting a sample to STAT-induced inhibitor of STAT function-1 in the presence of insulin, and by detecting inhibitory activity of STAT-induced inhibitor of STAT function-1 by a substance in the sample, as an index.

SSI-1 used in the screening method of the present invention is not limited to mouse SSI-1 shown in the sequence listing, but human SSI-1 successfully isolated by the inventors. For human SSI-1, see Biochem. Biophys. Res. Commun., 237:79-83 (1997).

In preferred embodiment of the present invention, a substance having hypoglycemic activity is detected by contacting a sample to cells expressing STAT-induced inhibitor of STAT function-1, and by detecting inhibitory activity of STAT-induced inhibitor of STAT function-1 expressed by the cells by the substance in the sample as an index. For cells to be used in the present invention, cells that express both SSI-1 and insulin receptor endogenously or exogenously and can respond to insulin biologically resulting in cell proliferation and sugar incorporation can be used. Spontaneous or transfected cells can be used. More specifically, the cells capable of incorpolating sugar, such as myocytes or adipocytes derived from human or mouse, transfected cells in which SSI-1 gene is introduced can be used. It is preferred that SSI-1 over-expressing transfectant produced in reference example 3 of the present invention is used.

For cell line to be used for preparing SSI-1 transfectant, a cell line that expresses insulin receptor endogenously or exogenously and can respond to insulin resulting in cell proliferation and sugar incorporation is preferred. More specifically, mouse fibroblast L929 cells, mouse 293T cells, rat L6 cells, human myocytes and human adipocytes can be used. It is preferred that mouse fibroblast L929 and mouse 293T cells are used.

In the expression of SSI-1, the expression vector can be prepared by inserting the DNA encoding SSI-1 into a proper vector having transcriptional regulator sequence such as promoter, operator and enhancer, terminator sequence, regulator sequence for SSI-1 gene and marker gene, and can be introduced into proper host cells. pEF-BOS plasmid or pCIBSD plasmid can be used as a vector when L929 cells or 293T cells are used as a host.

Calcium co-precipitation, transfection, electroporation, micro-injection and lipofection methods can be used for transfecting host cells with a recombinant DNA. Considering a size of a recombinant DNA and host cells to be used, the most proper technology can be selected and used.

In the screening of the present invention, a sample which is suspected to contain a substance having hypoglycemic activity can be used. For example, a lysate derived from a tissue or cells, a media cultured with a tissue or cells, a culture media of microbes, a component of microbes and synthesized compounds can be used.

In the screening of the present invention, for example, an inhibitory activity of a substance on SSI-1 can be confirmed by assessing a change of cell proliferation rate or sugar incorporation. In the preferred embodiment of the present invention, the method comprises (a) providing cells which express STAT-induced inhibitor of STAT function-1; (b) culturing the cells in an insulin-containing medium having added thereto a sample; (c) assessing the proliferation rate of the cells; and (d) detecting a substance having hypoglycemic activity by using the proliferation rate of the cells as an index. The proliferation rate between SSI-1 expressing- and non-expressing cells stimulated with insulin is different. The proliferation rate of SSI-1 expressing cells is significantly lower than that of SSI-1 non-expressing cells when both type of cells are cultured in the presence of insulin. Accordingly, an inhibitory activity on SSI-1 can be assessed by culturing said cells in an insulin-containing medium having added thereto a sample, followed by assessing the change of proliferation rate of said cells.

In SSI-1 over-expressing cells, not only cell proliferation but also various biological activities of insulin are also inhibited. Accordingly, it is considered that insulin dependent sugar incorporation of the cells is suppressed when SSI-1 is over-expressed in myocytes or adipocytes. In these conditions, a screening for a compound capable of recovering sugar incorporation can also be carried out.

BEST MODE FOR CARRYING OUT THE INVENTION

The present invention is illustratively described in the following with reference examples and examples, but they do not limit the scope of the present invention.

REFERENCE EXAMPLE 1

Measurement of BLOOD SUGAR LEVEL in SSI-1 Knocked-Out Mice

SSI-1 knocked-out mice were generated in BL6 mice by the similar method described in *Proc. Natl. Acad. Sci. USA*, 95:15577-15582 (1998). Blood sugar level in SSI-1 knocked-out (20 animals) and wild type BL6 mice (i.e., normal mice)(20 animals) were determined. Blood was drawn from hearts of the mice in both groups at between 10 a.m. and 11 a.m. The result is shown in Table 1 below.

TABLE 1

| | Blood sugar level (mg/dL) (Mean ± SE) |
|---|---|
| Wild type BL6 mice | 136.3 ± 26.5 |
| SSI-1 knocked-out mice | 84.1 ± 13.3 |

As shown in Table 1, the blood sugar level of SSI-1 knocked-out mice was significantly lower than that of wild type mice.

REFERENCE EXAMPLE 2

Differentiation of Embryonic Fibroblast Cells Derived from SSI-1 Knocked-Out Mice into Adipocytes Embryonic fibroblast cells were collected from SSI-1 knocked-out mice generated as described in reference example 1 above, and grown to 100% confluence on 48-well plates in Dulbecco's Modified Eagle's Medium (DMEM) containing 10% fetal calf serum (FCS), nonessential amino acids (GIBCO BRL), penicillin G, and streptomycin. Forty-eight hours after confluence, the culture medium was replaced by the induction medium (DMEM containing 10%

FCS, 5 ug/ml of insulin, 0.5 mM 3-isobutyl-1-methyl xanthine, and 1 uM dexamethasone) (day 0). After 48 hours incubation, the induction medium was replaced with a maintenance medium (DMEM supplemented with 10% FCS and 5 ug/ml of insulin), which was renewed every other day. After 6 days (day 6), adipose drops in the cells were stained with Oil Red-O and observed under a microscope.

Embryonic fibroblast cells derived from normal mice were also differentiated into adipocytes by the same method as described above, and adipose drops in the cells were stained with Oil Red-O and observed under a microscope.

As a result, it is confirmed that embryonic fibroblast cells derived from SSI-1 knocked-out mice showed burst induction of differentiation into adipocytes compared with that derived from normal mice.

REFERENCE EXAMPLE 3

Phosphorylation of IRS-1 in SSI-1 Expressing Cells and Embryonic Fibroblast Cells Derived from SSI-1 Knocked-Out Mice.

SSI-1 cDNA shown in SEQ ID No.1 in the Sequence Listing was digested with restriction enzyme XbaI and PvuII, and obtained restriction fragment was blunt-ended and then inserted into blunt-ended XaI site of mammalian expression vector pEF-BOS. The expression vector thus constructed is designated as pEF-BOS/SSI-1 hereinafter.

The constructed pEF-BOS/SSI-1 was introduced into mouse fibroblast cell line L929 together with pSV2Neo, which encodes neomycin resistant gene, at the ratio of 20:1, by electroporation method. The transfectants were selected in the growth medium containing 750 ug/ml of Geneticin (GIBCO BRL, USA) by using neomycin-resistance as an index. The transfectant (L929/SSI-1) thus obtained over-expresses SSI-1.

As a control, transfectant (L929/Neo) expressing only neomycin resistant protein was also obtained using pEF-BOS instead of pEF-BOS/SSI-1.

SSI-1 over-expressing cells (L929/SSI-1) and control transfected cells (L929/Neo) were cultured, respectively, in the medium containing 0.2% FCS for 16 hours. The cells were treated with 10 nM of insulin for 0, 10, 30 and 60 minutes, and recovered. The cells were then lysed with 20 mM Tris-HCl buffer (pH 7.5) containing 1% NP-40, 150 mM NaCl, 10 uM Na2VO4, 1 ug/mL leupeptin, 1 ug/mL pepstatin A, 1 mM dithiothreitol (DTT) and 1 mM (PMSF). The supernatants were collected and immunoprecipitated with anti-IRS-1 antibody to obtain immunecomplex. The immunecomplex thus obtained was resolved by SDS-PAGE followed by Western blot analysis with anti-phosphotyrosine antibody.

The Western blot analysis with anti-IRS-1 antibody was also performed.

Figure 1:
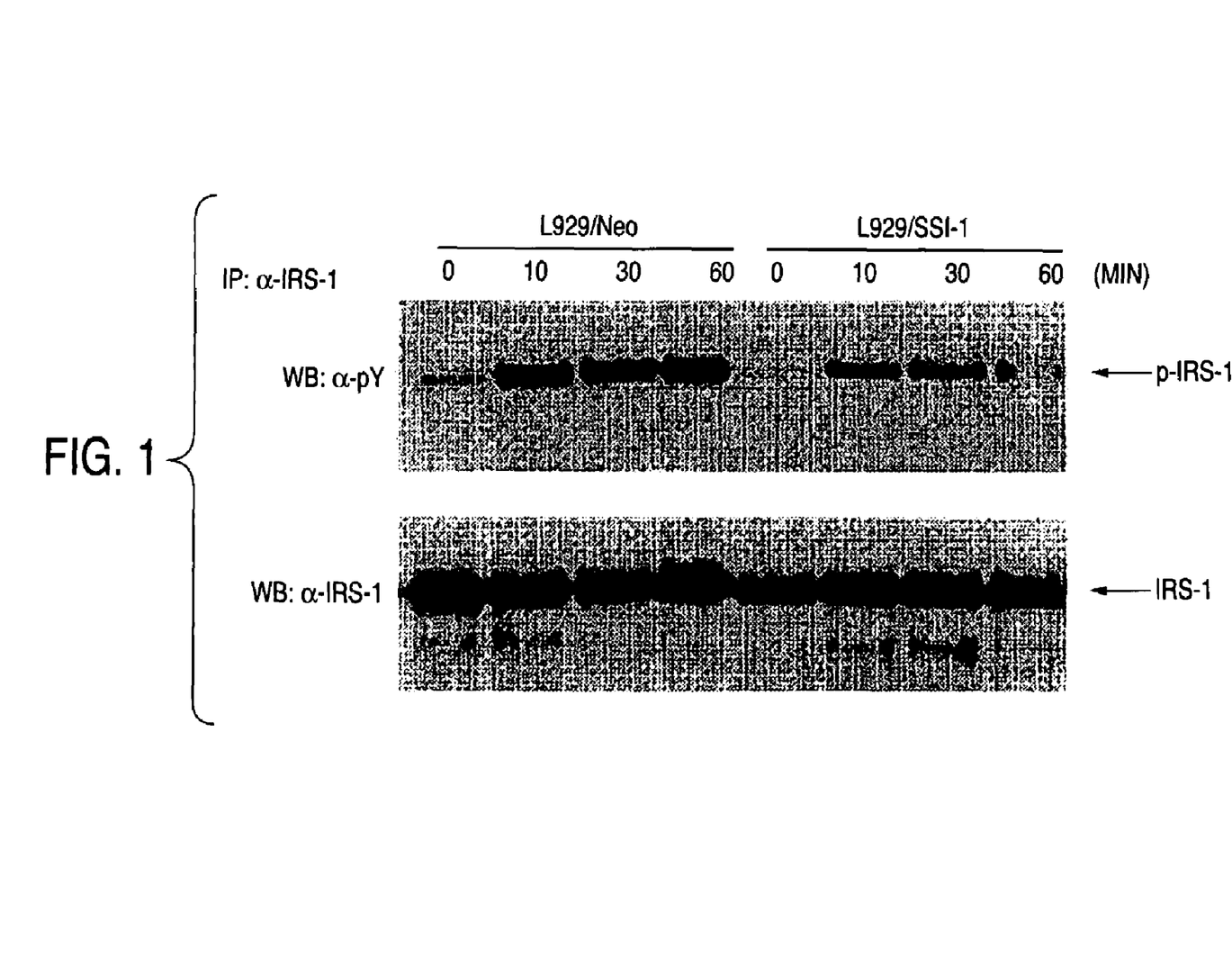
FIG. 1 shows the result of Western blot analysis, indicating a level of phosphorylation of IRS-1 after insulin stimulation in SSI-1 over-expressing cell line (L929/SSI-1) and reference cells (L929/neo). In the figure, IP:α-IRS-1 means immunoprecipitation with anti-IRS-1 antibody, WB:α-pY Western blot analysis with anti-phosphotyrosine antibody, WB:α-IRS-1 Western blot analysis with anti-IRS-1 antibody, and p-IRS-1 phosphorylated IRS-1.

The result of Western blot analysis is shown in FIG. 1.

The embryonic fibroblast cells derived from SSI-1 knocked-out and wild type mice, respectively, were stimulated with insulin and subjected to Western blot analysis by the same method described above. In these cases, cells were cultured in the medium containing 2% FCS for 48 hours, and stimulated with 5 ug/mL insulin for 0, 10, 60 and 180 minutes. The result of Western blot analysis is shown in FIG. 2.

As shown in FIG. 1, the phosphorylation of IRS-1 after insulin stimulation was reduced in SSI-1 over-expressing cells (L929/SSI-1) compared with control cells (L929/Neo).

Figure 2:
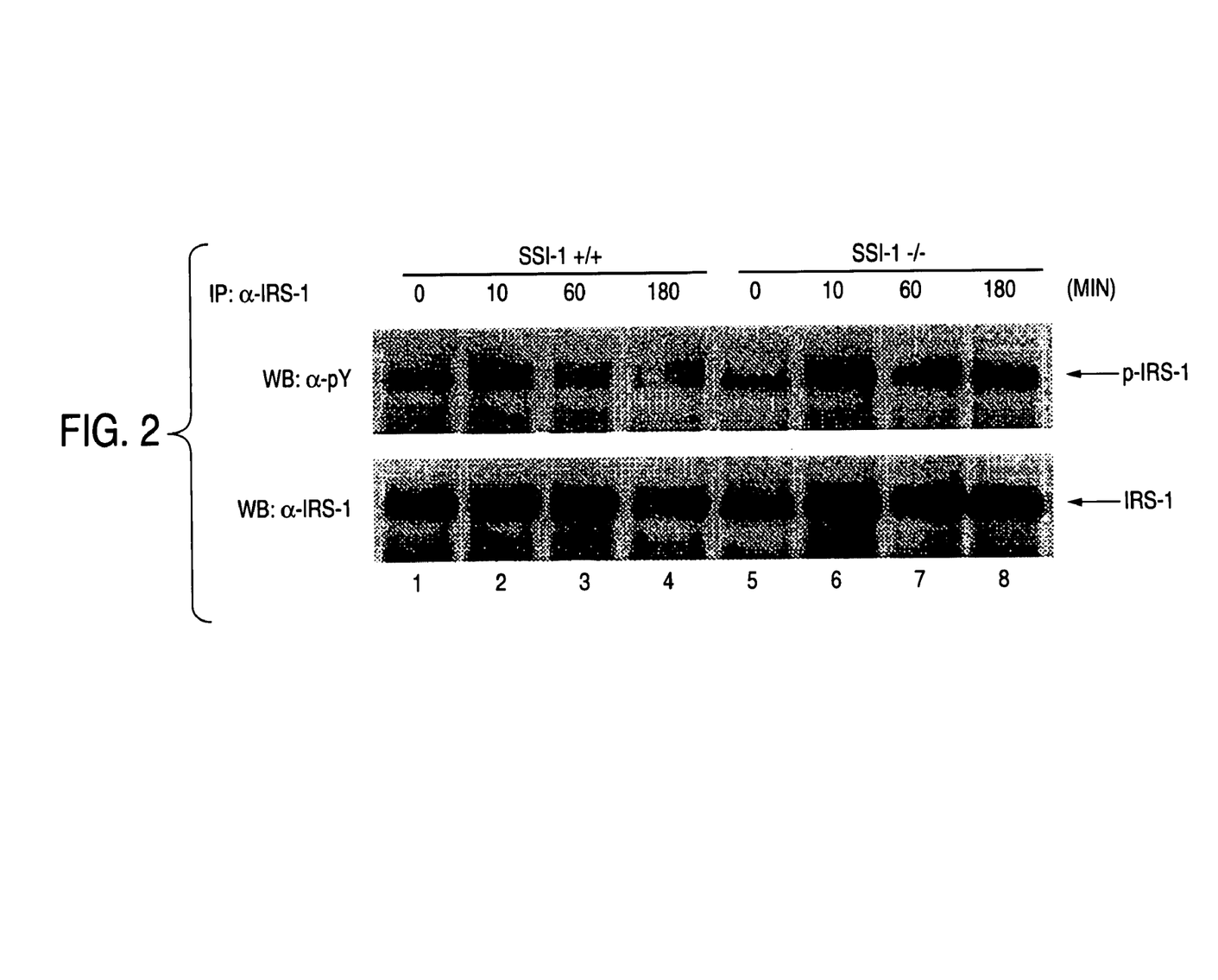
FIG. 2 shows the result of Western blot analysis, indicating a level of phosphorylation of IRS-1 after insulin-stimulation in fetal fibroblast cell line derived from SSI-1 knocked-out mice (SSI-1-/-) and fetal fibroblast cell line derived from wild mice (SSI-1+/+). In the figure, IP:α-IRS-1 means immunoprecipitation with anti-IRS-1 antibody, WB:α-pY Western blot analysis with anti-phosphotyrosine antibody, WB:α-IRS-1 Western blot analysis with anti-IRS-1 antibody, and p-IRS-1 phosphorylated IRS-1.

In contrast, as shown in FIG. 2, intense phosphorylation of IRS-1 after insulin stimulation was lasted in embryonic fibroblast cells (SSI-1−/−) derived from SSI-1 knocked-out mice compared with the cells (SSI-1+/+) derived from wild mice.

REFERENCE EXAMPLE 4

Studies of Molecular Mechanism of SSI-1 (Relation to Insulin Receptor (IR))

pEF-BOS/SSI-1 and pEF-BOS/IR were obtained by inserting SSI-1 and IR cDNA, respectively, into the PEF-BOS plasmid. The recombinant DNA was then introduced into 293T cells by calcium co-precipitation method, resulted in the formation of transfectants expressing the following cDNA(s) of (a)-(c).

(a) SSI-1,
(b) IR, and
(c) SSI-1 and IR.

In the case of transfectant (c), insulin stimulation was also performed.

Thirty-six hours after transformation, the cell lysate was prepared from each transfectant by the same method described in reference example 3, and immunoprecipitated with anti-IR antibody. The immunecomplex thus obtained was resolved by SDS-PAGE followed by Western blot analysis with anti-phosphotyrosine antibody to study a level of phosphorylation of IR.

Both the cell lysates before immunoprecipitation and the immunecomplexes obtained by using anti-IR antibody were subjected to Western blot analysis with anti-SSI-1 antibody to study an interaction between IR and SSI-1. The result is shown in FIG. 3.

In Western blot analysis with anti-SSI-1 antibody using the immunecomplex obtained with anti-IR antibody, the band corresponding to SSI-1 could not be found, thus the interaction between SSI-1 and IR was not confirmed. In the case of Western blot analysis with anti-phosphotyrosine antibody, the phosphorylation of IR itself was found in the transfectant (b) expressing IR only. In the case of transormant (c) that expresses both SSI-1 and IR, the phosphorylation of IR was also found and augmented by insulin stimulation.

Figure 3:
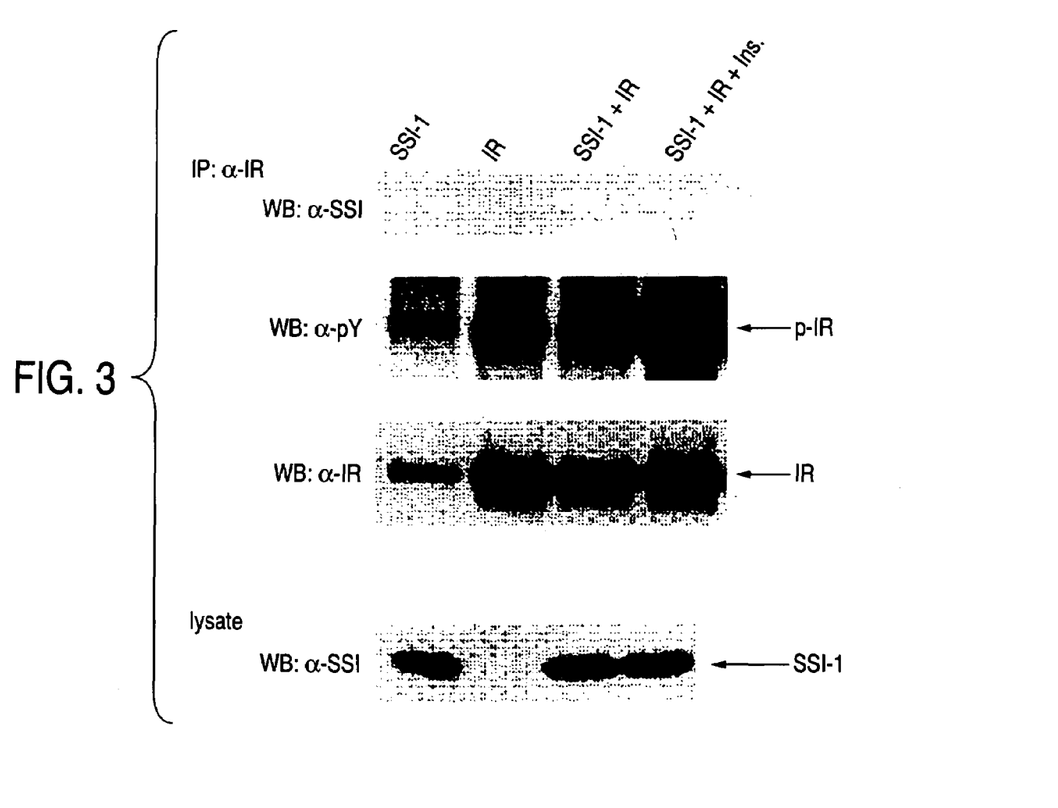
FIG. 3 shows the result of Western blot analysis, indicating a level of phosphorylation of IR in transfected cells expressing SSI-1 (SSI-1), transfected cells expressing IR (IR), transfected cells expressing both SSI-1 and IR (SSI-1+IR) and insulin stimulated SSI-1+IR. In the figure, IP:α-IR means immunoprecipitation with anti insulin receptor antibody, WB:α-SSI Western blot analysis with anti-SSI antibody, WB:α-pY Western blot analysis with anti-phosphotyrosine antibody, WB:α-IR Western blot analysis with anti insulin receptor antibody, and p-IR phosphorylated IR. The figure also shows the result of Western blot analysis with anti-SSI-1 antibody without immunoprecipitation of cell lysates from each transfectant.

The result shown in FIG. 3 indicated that SSI-1 neither bound to insulin receptor nor suppressed the kinase activity of insulin receptor.

REFERENCE EXAMPLE 5

Studies of Molecular Mechanism of SSI-1 (Relation to JAK and IRS-1)

pEF-BOS/IRS-1, pEF-BOS/JAK and pEF-BOS/SSI-1 were obtained by inserting the cDNA of IRS-1, JAK and SSI-1, respectively, into the pEF-BOS plasmid. The recombinant DNA obtained was then introduced into 293T cells by using calcium co-precipitation method, resulted in the formation of transfectant expressing each cDNA(s) shown in the following (d)-(f).

(d) IRS-1,
(b) IRS-1 and JAK, and
(c) IRS-1, JAK and SSI-1.

(Although Jak1 and Jak2 are known to be involved in JAK kinase family, Jak1 was used in the present invention.)

The cell lysate was prepared from each transfectant by the same method described in reference example 3, and immunoprecipitated with anti-IRS-1 antibody. The immunecomplex thus obtained was resolved by SDS-PAGE followed by Western blot analysis with anti-phoshotyrosine antibody to study a level of phosphorylation of IRS-1. The anti-JAK antibody was also used in the Western blot analysis.

The cell lysate before immunoprecipitation was also subjected to Western blot analysis with anti-SSI-1 or anti-JAK antibody to study an interaction between IRS-1 and SSI-1. The result is shown in FIG. 4.

The result of Western blot analysis with anti-phosphotyrosine antibody indicated that the phosphorylation of IRS-1 was very little in the transfectant expressing IRS-1 only (d), but augmented in the transfectant expressing both IRS-1 and JAK (e). In the transormant (f) that expresses IRS-1, JAK and SSI-1, the phosphorylation of IRS-1 was lower than that in the transfectant (e).

The result of Western blot analysis with anti-SSI-1 antibody using the cell lysate without immunoprecipitation indicated that the interaction between IRS-1 and JAK was found in the transfectant (e) expressing both IRS-1 and JAK, but was reduced in the transfectant (f) expressing SSI-1 in addition to IRS-1 and JAK.

Figure 4:
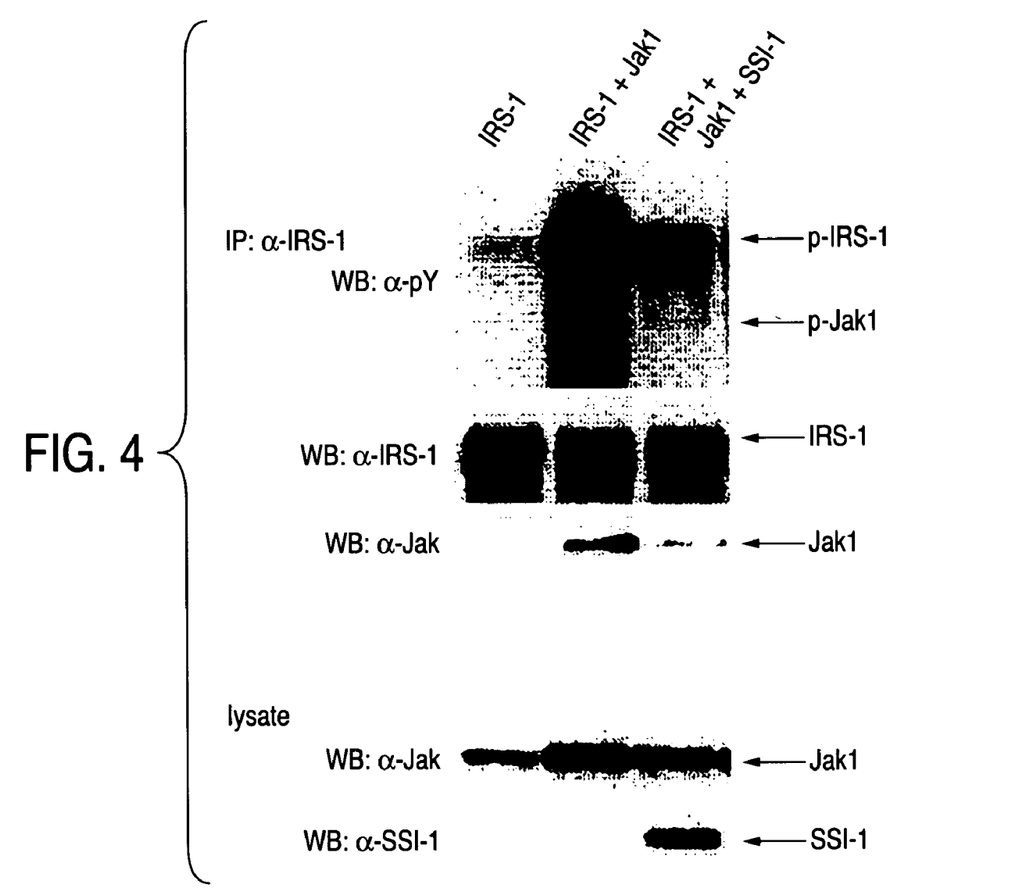
FIG. 4 shows the result of Western blot analysis, indicating a level of phosphorylation of IRS-1 and an interaction between IRS-1 and JAK in transfected cells expressing IRS-1 (IRS-1), transfected cells expressing IRS-1, JAK and SSI-1 (IRS-1+JAK1+SSI-1). In the figure, IP:α-IRS-1 means immunoprecipitation with anti-IRS-1 antibody, WB:α-pY Western blot analysis with anti-phosphotyrosine antibody, WB:α-IRS-1 Western blot analysis with anti-IRS-1 antibody, WB:α-Jak Western blot analysis with anti-JAK-1 antibody, WB:α-SSI Western blot analysis with anti-SSI antibody, p-IRS-1 phosphorylated IRS-1, and p-Jak-1 phosphorylated Jak-1. The figure also shows the result of Western blot analysis with anti-JAK-1 antibody and anti-SSI-1 antibody without immunoprecipitation of cell lysates from each transfectant.

The result shown in FIG. 4 indicated that SSI-1 suppressed the phosphorylation of IRS-1 through binding to JAK associated with insulin receptor and suppressing JAK kinase activity.

EXAMPLE 1

Screening of a Substance Having Hypoglycemic Activity

Figure 5:
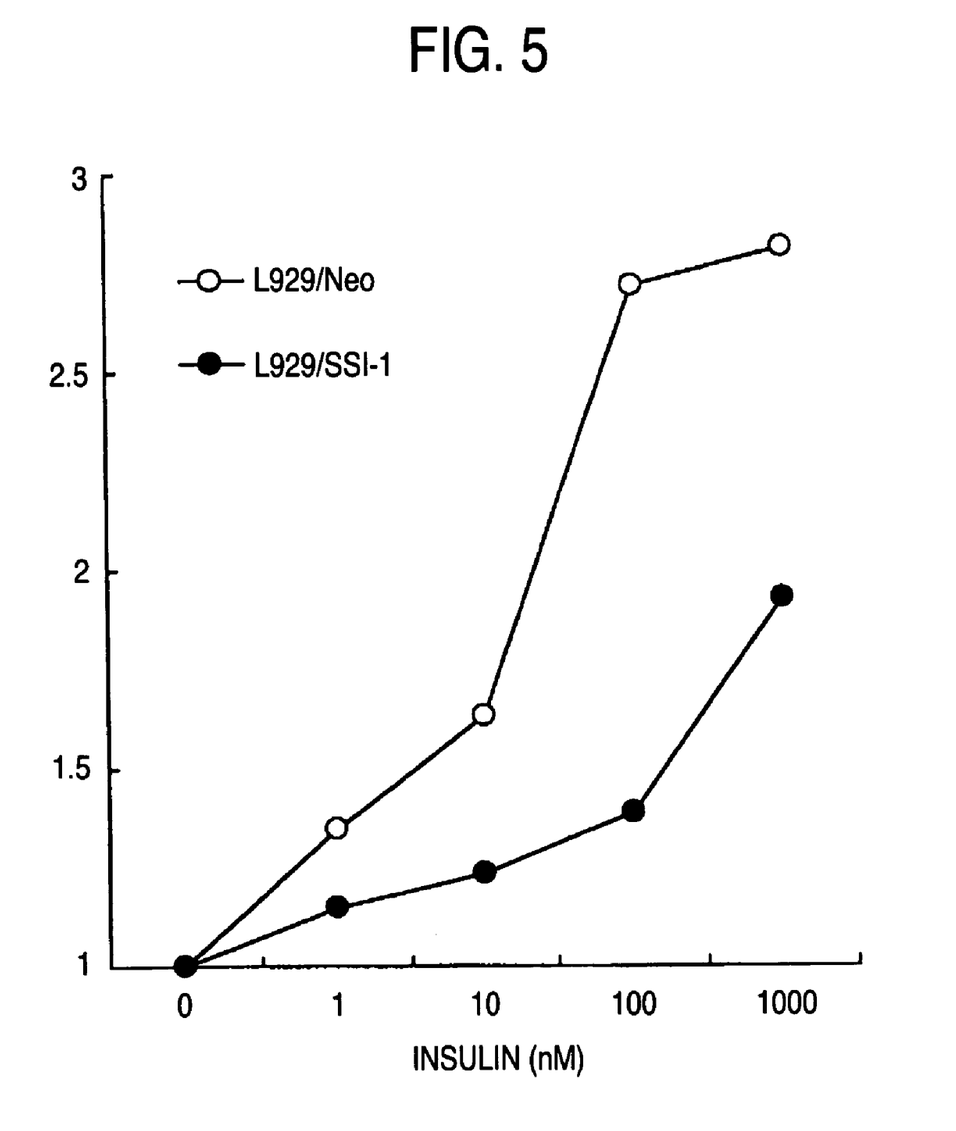
FIG. 5 shows the rate of cell proliferation after insulin stimulation in SSI-1 over-expressing cell line (L929/SSI-1) and reference cells (L929/neo). In the figure, -○- means the rate of cell proliferation of reference cells and -●- SSI-1 over-expressing cells. The axis shows insulin concentration (nM) in the medium. The column is demonstrated as relative cell proliferation rate against the cell number in the absence of insulin.

SSI-1 over-expressing cells (L929/SSI-1) prepared in reference example 3 were plated at 30,000 cells/well in 96-well plates with the medium (DMEM containing 0.5% FCS) containing no or various concentrations of insulin. After 18 hours incubation, bromodeoxyuridine (BrdU) was added to the wells. After 6 hours (total 24 hours incubation), the cell number was measured using "Cell Proliferation ELISA BrdU Kit" (Boehringer mannheim). FIG. 5 shows the cell proliferation rate against the cell number in the absence of insulin.

As a control, the transfectant cells (L929/Neo) were also cultured in the medium with or without insulin, and the relative proliferation rate after 24 hours incubation was calculated and shown in FIG. 5.

The cell number was increased depending upon insulin concentration in both cell lines. The cell proliferation rate was reduced by approximate 50% in SSI-1 over-expressing cells (L929/SSI-1) as compared to the control cells (L929/Neo), indicating that SSI-1 suppressed insulin-induced cell proliferation. Accordingly, a substance having hypoglycemic activity through inhibiting SSI-1 activity can be screened by culturing SSI-1 over-expressing cells (L929/SSI-1) in an insulin-containing medium having added thereto a sample, followed by assessing the proliferation rate of said cells.

INDUSTRIAL APPLICABILITY

The present invention provides a method for screening a substance, which has a hypoglycemic activity through a new molecular mechanism inhibiting SSI-1 and could be a therapeutic agent for diabetes with insulin resistance. By using the method of the present invention, a substance capable of regulating a function of a molecule involved in insulin signaling pathway, and could be a therapeutic agent for diabetes with insulin resistance can be screened.

What is claimed is:

1. A screening method for identifying a substance having STAT-induced inhibitor of STAT function-1 (SSI-1)-dependent hypoglycemic activity, comprising:
    (a) providing cells which express SSI-1 and cells which do not express SSI-1;
    (b) contacting a candidate substance with said cells each cultured in the presence of insulin;
    (c) assessing the cell proliferation rate of said cells; and
    (d) comparing the effect of the candidate substance on the cell proliferation rate of the cells which express SSI-1 with the effect of the candidate substance on the cell proliferation rate of the cells which do not express SSI-1, thereby determining whether said candidate substance has SSI-1 dependent hypoglycemic activity.

2. The method of claim 1, wherein said cells which express SSI-1 have a lower proliferative rate than said cells which do not express SSI-1 in an insulin-containing medium that does not comprise a substance having SSI-1 dependent hypoglycemic activity.

3. The method according to claim 1, wherein said cells which express SSI-1 are transfectants which over-express SSI-1.

4. The method according to claim 2, wherein said cells which express SSI-1 are transfectants which over-express SSI-1.

5. The method of claim 3, wherein the cells are L929 cells.

6. The method of claim 1, wherein cell proliferation rate is determined by measuring incorporation of bromodeoxyuridine (BrdU).

* * * * *